(12) United States Patent
Bogdanova et al.

(10) Patent No.: US 8,680,042 B2
(45) Date of Patent: Mar. 25, 2014

(54) METHODS OF TREATING SICKLE CELL ANEMIA-RELATED CONDITIONS WITH MK-801 OR MEMANTINE

(75) Inventors: Anna Yulienva Bogdanova, Zürich (CH); Max Gassman, Zürich (CH); Jeroen Goede, Wetzikon (CH)

(73) Assignee: Universität Zürich Prorektorat MNW, Zürich (CH)

( * ) Notice: Subject to any disclaimer, the term of this patent is extended or adjusted under 35 U.S.C. 154(b) by 0 days.

(21) Appl. No.: 13/265,709

(22) PCT Filed: Apr. 18, 2010

(86) PCT No.: PCT/EP2010/055077
§ 371 (c)(1),
(2), (4) Date: Jan. 19, 2012

(87) PCT Pub. No.: WO2010/121973
PCT Pub. Date: Oct. 28, 2010

(65) Prior Publication Data
US 2012/0116060 A1    May 10, 2012

(30) Foreign Application Priority Data
Apr. 23, 2009   (EP) .................................... 09005683

(51) Int. Cl.
*A01N 61/00* (2006.01)
*A61K 31/00* (2006.01)
(52) U.S. Cl.
USPC ............................................................ 514/1

(58) Field of Classification Search
None
See application file for complete search history.

(56) References Cited

PUBLICATIONS

Zempsky W. et al. "(399) Low-dose Ketamine for vasoocclusie pain in pediatric patients with sicle cell disease: A case series" Journal of Pain, Saunders, Philadelphia vol. 9, No. 4, Apr. 1, 2008 p. 75, XP025871572.
Wong et al. "The Anticonvulsant MK-801 is a Potent N Methyl-D-Aspartate Antagonist" Proceedings of the National Academy of Sciences of the United States of America vol. 83, No. 18, 1986, pp. 7104-7108, XP002585977.
Mosca et al. "17$^{th}$ International Symposium of the European Association for Red Cell Research, EARCR 2009, Triuggio, Milano, Italy, Apr. 23-27, 2009" Clinical Biochemistry, Elsevier Inc, US CA LNKD vol. 42, No. 18, Dec. 1, 2009, pp. 1851-1863, XP026782104.

*Primary Examiner* — Robert Landsman
(74) *Attorney, Agent, or Firm* — Cozen O'Connor

(57) ABSTRACT

Sickle cell anemia is a genetic disease characterized by red blood cells that assume an abnormal, rigid, sickle shape. Acute complications of Sickle cell anemia are treated symptomatically with analgesics and transfusions, and a prophylactic treatment of sickle cell crisis is long term application of hydroxyurea. According to the present invention, an N-methyl D-aspartate receptor (NMDAR) blocker is used for the treatment of sickle cell anemia and for manufacture of a medicament for the treatment of sickle cell anemia. Moreover, a method for screening for a compound effective in the treatment of sickle cell anemia comprises contacting a candidate compound with the NMDAR and selecting said candidate compound as effective if it is found to selectively reduce activity of the NMDAR.

8 Claims, 3 Drawing Sheets

METHODS OF TREATING SICKLE CELL ANEMIA-RELATED CONDITIONS WITH MK-801 OR MEMANTINE

This application is the U.S. national stage of PCT International Application No. PCT/EP2010/055077, filed Apr. 18, 2010, which claims priority of European Application No. 09005683.9, filed Apr. 23, 2009.

FIELD OF THE INVENTION

This invention relates to the treatment of sickle cell anemia, using blockers of NMDA.

BACKGROUND OF THE INVENTION

The N-methyl D-aspartate receptor (NMDAR) is an ionotropic receptor for glutamate. Blockers of NMDAR have been used as anesthesia and for treatment of traumatic brain injury, stroke, and neurodegenerative diseases such as Alzheimer's, Parkinson's, and Huntington's.

This invention focuses on the treatment of sickle cell anemia, a genetic disease characterized by red blood cells that assume an abnormal, rigid, sickle shape. Acute complications of Sickle cell anemia are treated symptomatically with analgesics and transfusions. A prophylactic treatment of sickle cell crisis is long term application of hydroxyurea. Further treatment options are very desirable.

SUMMARY OF THE INVENTION

The present invention relates to a method of treating sickle cell anemia, using blockers of the NMDAR. Furthermore the invention relates to blockers of the NMDAR for use in the treatment of sickle cell anemia.

The invention further relates to a method of screening for a compound effective in the treatment of sickle cell anemia, comprising contacting a candidate compound with the NMDAR and choosing candidate compounds which selectively reduce activity of the NMDAR. The invention further relates to compounds selected by these methods of screening.

DETAILED DESCRIPTION OF THE INVENTION

Figure 1:
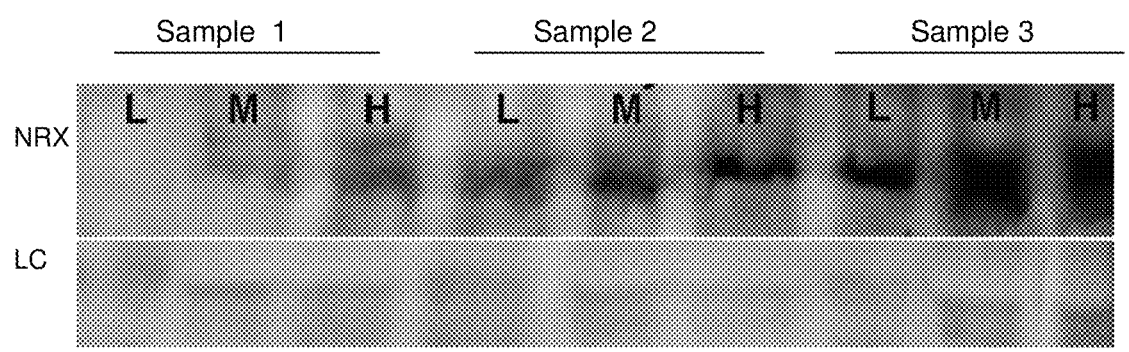
FIG. 1: Samples 1-3 are from three patients with sickle cell anemia. Shown is the specific staining against the NR1 subunit of the NMDA receptor (NRX) and the loading control (LC) of the light (L), middle (M) and high density (H) subpopulations of erythrocytes.
Figure 2:
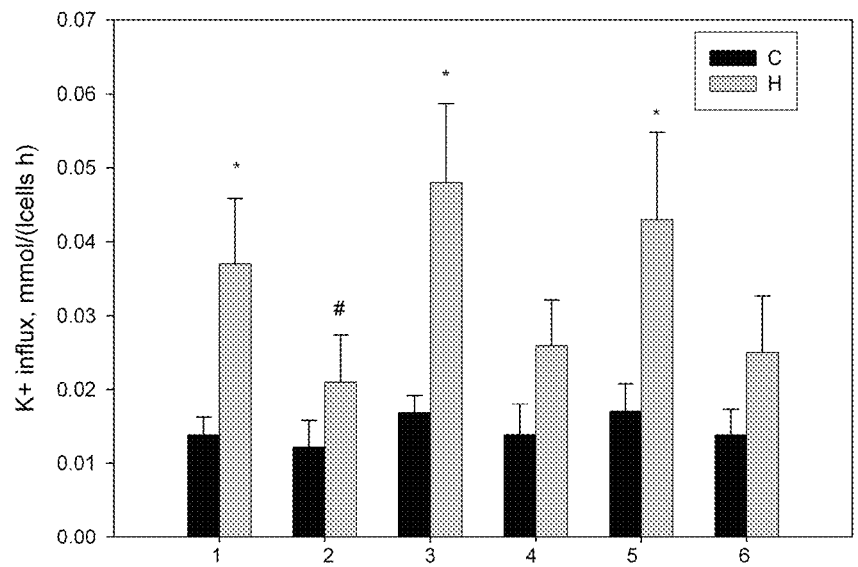
FIGS. 2A and 2B: Potassium and calcium fluxes through the NMDA receptor in erythrocytes of healthy donors (C) and patients with sickle cell anemia (H). 2A: Unidirectional $K^+$ influx measured in chloride-free Na-methane sulfate medium in the presence of 100 µM ouabain, the inhibitor of $Na_1K$-ATPase. Conditions corresponding to the numbers at the X axis: (1) control; (2) 50 µM memantine chloride (Sigma-Aldhdge); (3) 100 µM NMDA; (4) NMDA+memantine chloride; (5) 2 µM prostaglandine E2 (PGE2); (6) PGE2+memantine chloride. * denotes p<0.05 compared to the corresponding values in healthy donor's erythrocytes, # stands for p<0.05 compared to the corresponding non-treated control. Data are means±SEM for 6-7 individuals. 2B: Unidirectional $Ca^{2+}$ influx in erythrocytes of a single HbSS patient measured on 3 different occasions and in three healthy donors. Conditions indicated in numbers at the X axis are: (1) non-treated control; (2) 100 µM NMDA; (3) 100 µM NMDA and 50 µM MK-801. * denotes p<0.05 compared to the corresponding healthy donors' samples.
Figure 2:
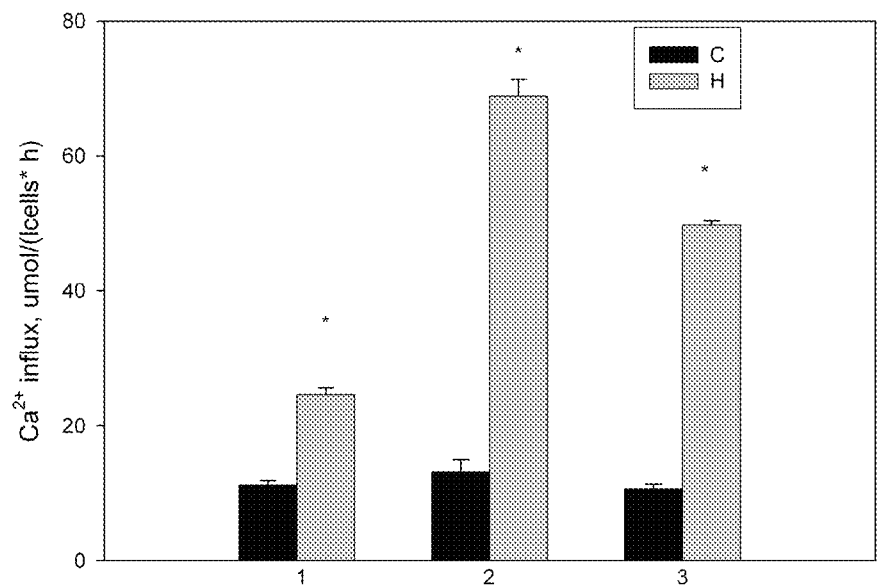

The present invention relates to a method of treating sickle cell anemia, comprising administering blockers of the NMDAR, and the use of such blockers in said treatment and in the manufacture of medicaments for treating sickle cell anemia.

The action of the NMDAR can be blocked by administration of antibodies or antibody fragments directed against the NMDAR, of molecules that affect the protein or mRNA expression of the NMDAR (sRNA; miRNA), as well as of small molecules that interfere with the binding of ligands to the NMDAR (e.g. blocking the binding site of the neurotransmitter glutamate or the glycine site; or inhibiting NMDAR by binding to allosteric sites or blocking the ion channel by binding to a site within it). A further way to prevent binding to the NMDAR is to use soluble NMDAR or fragments thereof.

Examples of NMDAR blockers according to the invention are disclosed in the following. However, the invention is not restricted to the blockers disclosed therein, but extends to all blockers of NMDAR.

Preferred blockers of NMDAR according to the invention are:

Soluble NMDAR or fragments thereof

Antibodies that bind to NMDAR, antigen binding fragments of an antibody (e.g. Fab fragments) or antibody-like molecules (e.g. repeat proteins) which by binding to NMDAR block its biological activity. Antibodies against NMDAR are known in the art and include the well characterized antibody NMDA NR 1 Pan Antibody, mouse monoclonal, Novus biologicals, NB 300-118.

Virus-like particles loaded with NMDAR or fragments thereof and therefore inducing an antibody response directed against NMDAR with the effect to block its biological activity Antisense molecules for downregulation of NMDAR. These antisense molecules are approximately 12-50 nucleotides in length and encode a given sequence found in the exons or introns of NMDAR. Moreover, antisense molecules containing a sequence of the NMDAR promoters and binding within the promoter region may be used. Finally, antisense molecules binding in the 3' UTR-non translated regions of NMDAR are contemplated Small molecules that block the biological activity of NMDAR. Small molecules contemplated are synthetic compounds up to a molecular weight of approximately 1000 which have suitable physiological activity and pharmacological properties making them useful for the application as medicaments. Such small synthetic molecules are, for example, found by the screening method of the present invention described below. Alternatively, such small molecules are designed by molecular modelling taking into account possible binding sites of NMDAR.

Proteins and protein analogs which bind NMDAR and thereby inhibit its biological activity, for example, synthetic proteins or protein analogs which mimic the variable region of binding and/or neutralizing antibodies, or antibodies that mimic a binding pocket of the NMDAR. Likewise small molecules could be applied, which mimic the variable region of binding and/or neutralizing antibodies, or that mimic a binding pocket of the NMDAR.

Particularly preferred blockers are:
Amantadine (Novartis, Actavis, Pharmascience)
Dextromethorphane, Dextrorphan (e.g. Johnson & Johnson)
Ibogaine
Ketamine (e.g. Javeline Pharmaceuticals)
Nitrous oxide
Phencyclidine
Riluzole (Sanofi-Aventis)
Tiletamine
Memantine (Allergan, Daiichi Sankyo, Forest Laboratories, Lundbeck)
Dizocilpine (MK-801)
Aptiganel (Cerestat, CNS-1102)
Remacimide
HU-211, an enantiomer of the potent cannabinoid HU-210
7-Chlorokynurenate
DCKA (5,7-dichlorokynurenic acid)
Kynurenic acid, a naturally occurring antagonist
1-Aminocyclopropanecarboxylic acid (ACPC)
Lacosamide
AP7 (2-amino-7-phosphonoheptanoic acid)
APV (R-2-amino-5-phosphonopentanoate)
CPPene (3-[(R)-2-carboxypiperazin-4-yl]-prop-2-enyl-1-phosphonic acid)
flupirtine (Adeona Pharmaceuticals, Inc.)
orphenadrine (Actavis, Akorn)
Neu2000KL (Amkor Pharma, Neurotech)
AZD6765 (Astra-Zeneca)
AM-101 (Auris Medical)
Indantadol (Chiesi Farmaceutici, Vernalis)
C-10003 (Concert Pharmaceuticals)
EVT101, EVT102, EVT103 (Evotec)
Radiprodil (Forrest Laboratories)
Gacyclidine (1-[(1R,2S)-2-methyl-1-thiophen-2-yl-cyclohexyl]piperidine; Neureva)
CNS 5161 (2-(2-chloro-5-methylsulfanyl-phenyl)-1-methyl-1-(3-methylsulfanyl-phenyl)guanidine; Paion)
Dexanabinol and other dextrocannabinoid compounds (Pharmos)
CR3394 (Rottapharm)
Felbamate ((3-carbamoyloxy-2-phenyl-propyl) carbamate; Schering-Plough)
TXT0300 (Traxion Therapeutics)
AV101 (7-chloro-4-oxo-1H-quinoline-2-carboxylic acid; VistaGen Therapeutics)
YT1006 (Yaupon Therapeutics)
Most preferred blockers are:
Memantine (Allergan, Daiichi Sankyo, Forest Laboratories, Lundbeck)
Dizocilpine (MK-801)

One aspect of the invention relates to a method of preventing and treating sickle cell anemia, comprising administering blockers the NMDAR as defined hereinbefore in a quantity effective against sickle cell anemia to a mammal in need thereof, for example to a human requiring such treatment. For the administration, the blocker is preferably in the form of a pharmaceutical preparation comprising the blocker in chemically pure form and optionally a pharmaceutically acceptable carrier and optionally adjuvants. The blocker is used in an amount effective against sickle cell anemia. The dosage of the active ingredient depends upon the species, its age, weight, and individual condition, the individual pharmacokinetic data, and the mode of administration. In the case of an individual having a body-weight of about 70 kg the daily dose administered is from approximately 0.001 mg/kg to approximately 10 mg/kg, preferably from approximately 0.05 mg/kg to approximately 1 mg/kg, of a blocker of NMDAR. If memantine hydrochloride is applied in humans, a maximal daily dose of 20 mg is administered in adults. To avoid adverse effects a starting dose of 5 mg daily is recommended. The dosage should be increased weekly by 5 mg a day till the maximal dosage (20 mg daily) has been reached. In case of moderate renal insufficiency (Creatinin-Clearance 40-60 ml/min/1.73 m2) the maximal dosage should be reduced to 10 mg daily.

Pharmaceutical compositions for enteral administration, such as nasal, buccal, rectal or, especially, oral administration, and for parenteral administration, such as subcutaneous, intravenous, intrahepatic or intramuscular administration, are especially preferred. The pharmaceutical compositions comprise from approximately 1% to approximately 95% active ingredient, preferably from approximately 20% to approximately 90% active ingredient.

For parenteral administration preference is given to the use of solutions of the blockers of NMDAR, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal/intraperitoneal and intravenous applications are also considered, for example using a transdermal patch, which allows administration over an extended period of time, e.g. from one to twenty days.

Intravenous or subcutaneous application are particularly preferred.

Another aspect of the invention relates to the use blockers of NMDAR as described hereinbefore in the treatment of sickle cell anemia, and in the manufacture of medicaments for treating these diseases.

Medicaments according to the invention are manufactured by methods known in the art, especially by conventional mixing, coating, granulating, dissolving or lyophilizing.

The blockers of NMDAR can be administered alone or in combination with one or more other therapeutic agents, possible combination therapy taking the form of fixed combinations of a blocker NMDAR and one or more other therapeutic agents known in the treatment of sickle cell anemia, the administration being staggered or given independently of one another, or being in the form of a fixed combination.

Possible combination partners considered are vitamins B9 and B12 and other medicaments minimizing plasma homocysteine levels. One more group of compounds that could be considered as possible partners are blockers of Gardos channels (such as ICA-17043, see Blood. 2003; 101: 2412-2418) and inhibitors of the K+—Cl— cotransporter including magnesium salts.

The invention further relates to a method of screening for a compound effective in the treatment of sickle cell anemia comprising contacting a candidate compound with NMDAR and choosing candidate compounds which selectively reduce the activity of the NMDAR. The invention further relates to compounds selected by these methods of screening.

Blockers of NMDAR activity are identified by contacting the NMDAR with a candidate compound. A control assay with the corresponding NMDAR in the absence of the candidate compound is run in parallel. A decrease in activity in the presence of the candidate compound compared to the level in the absence of the compound indicates that the candidate compound is a NMDAR blocker. NPC-16 Patchliner or Syncropatch 96 (Nanion Technologies GmbH) is optimal for screening of the candidate NMDAR blockers specifically on human erythrocytes.

Antibodies against the NMDAR can be generated e.g. by immunization of mice.

Concepts and Evidence Behind the Invention

In vitro studies showed that erythrocytes of patients with sickle cell anemia contain more NMDA receptor than that of healthy donors and that these receptors are predominantly retained in the cell fraction prone or already undergoing sickling (uncontrolled irreversible shrinkage). This cell population looses cell water and $K^+$ due to the high permeability of the cell membrane to $Ca^{2+}$ mediated by the NMDA receptor. This leads to the conclusion that blocking the NMDA receptor may prevent irreversible shrinkage of erythrocytes of patients with sickle cell anemia.

Experiments Performed

The following experiments were conducted using fresh-isolated human erythrocytes of HbSS patients and healthy subjects.

Experiment 1

Localization of the NMDA receptors in erythrocytes of patients and healthy subjects was studied using immunoblotting (FIG. 1) and in cells treated with a selective irreversible blocker of the NMDA receptor 3H-MK-801. The number of the MK-801 binding sites per erythrocyte was assessed in sub-populations of cells with different densities (potential age groups). To do so the erythrocyte suspensions in the medium containing (mM) 145 NaCl, 4KCl, $1CaCl_2$, 0.15 $MgCl_2$, 10 sucrose, 10 glucose, 10 Tris-HCl (pH 7.4) were incubated at room temperature for 30 min in the presence of 3H-MK-801. Thereafter the cells were washed from external radioactivity and separated on the Percoll density gradient (see Lutz et al., Biochim Biophys Acta Mar. 5, 1992; 1116 (1):1-10). Cell sub-populations of different densities were then isolated, washed and lysed with distilled water. Membranes were then collected by centrifugation, dissolved in the scintillation fluid (Quicksafe A, Zinsser Analytic) and the amount of 3H-MK-801 assessed by beta counter and normalized to the amount of cells. Receptors were equally distributed between reticulocytes and young cells (8±1 receptors per cell), mature cells (8±3) dense senescent cell population (7±2). In patients with HbSS the number of receptor copies per cell was higher in all cell populations (50±2, 17±5 and 19±10 receptors per cell in young, mature and senescent sub-populations respectively). When blocker-free the young cells were the first to undergo sickling and shrinkage as the receptor is predominantly present in the dense population (cells prone to sickling).

Experiment 2

Fluxes via the nonselective cation channel of the NMDA receptor were assessed using radioactive tracer kinetics. 86Rb was used as a radioactive tracer for $K^+$ and 45Ca as a tracer for $Ca^{2+}$. Fluxes through the red cell membrane were measures in the medium containing (mM) 145 Na-methane sulfate, 4 K-gluconate, 1 Ca-gluconate, 10 sucrose, 10 glucose and 10 HEPES-Tris (pH 7.4) in the presence of 100 μM L-arginine and 100 μM ouabain. Details of the flux measurement may be found elsewhere (e.g. Bogdanova et al., J Membr Biol. 2003; 195(1):33-42). Erythrocytes of the HbSS patients showed higher passive $K^+$ and $Ca^{2+}$ fluxes that may be blocked by MK-801 (50 μM) or the reversible inhibitor of the NMDA receptor used in treatment of Alzheimer disease, memantine (50 μM). Fluxes of both cations are further stimulated by NMDA (100 μM) or prostaglandine E2 (2 μM). Both NMDA- and PGE2-sensitive increase in fluxes could be blocked by MK-801 or memantine. Fluxes through the NMDA receptors were significantly higher in patients with sickle cell anemia during the flue incidents which corresponded to the anemic crisis and hospitalization.

Experiment 3

High levels of the NMDA receptors and sensitization of HbSS patients' erythrocytes to NMDA treatment was shown. There was no direct correlation of the abundance of receptors in red cells and the amount of reticulocytes (routine blood status analysis), but rather with specific hematological disorders such as sickle cell anemia. Functional activity of the receptors was assessed by measuring K+(86Rb) influx through the receptor channels and 3H-MK-801 finding studies. Routine screening of control individuals for the receptor expression in erythrocytes revealed that one of them with abnormally high number of receptor copies had beta-thalassemia minor.

Experiment 4

Figure 3:
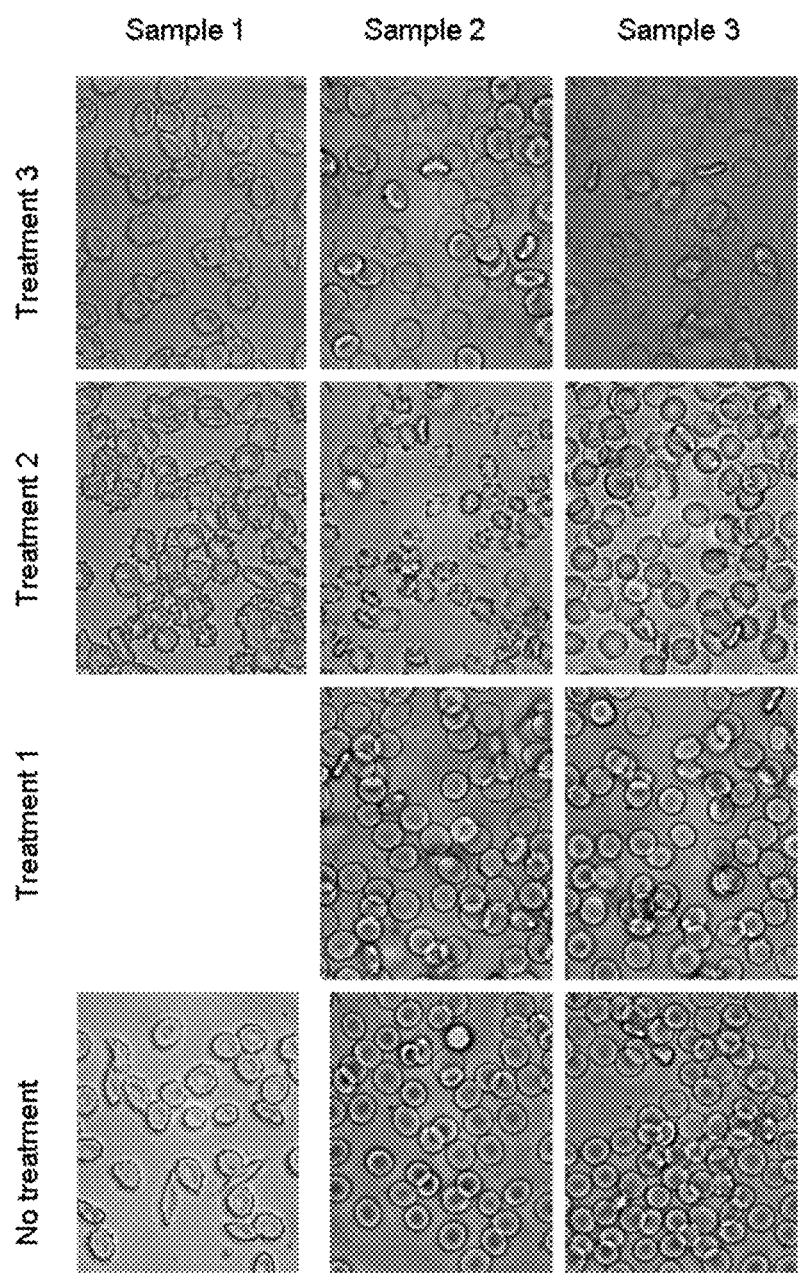
FIG. 3: The examples of morphological changes in erythrocytes caused by agonists and antagonists of the NMDA receptor depending on the receptor availability and HbSS presence. Sample 1 is a sample from a sickle cell patient, sample 2 is from a person with high levels of NMDA receptors and reticulocytes and sample 3 is from a person with low levels of receptors. Treatment 1 denotes administration of 50 µM memantine (sample 2) or MK-801 (sample 3), treatment 2 stands for 1 mM NMDA addition, treatment 3 shows morphological changes in the cells pre-treated with mennantine/MK-801 and then exposed to 1 mM NMDA.

Abnormally high sensitivity of the HbSS erythrocytes to NMDA treatment can be followed microscopically as changes in cell morphology. Shown in FIG. 3 are the cells of healthy donors and HbSS patients exposed to 1 mM NMDA with and without pre-treatment with 50 μM of MK-801/memantine.

Clinical Study, Treatment of Patients with Sickle Cell Anemia with NMDAR Blocker (Suggested Study)

A prospective phase II clinical feasibility study in human sickle cell patients with a NMDAR blocker can be performed as follows: It starts with an oral treatment with memantine hydrochloride. The maximal daily dose is analogous to the clinical experiences in Alzheimer disease, i.e. 20 mg with a starting dose of 5 mg daily and if tolerability is good a weekly increase of 5 mg a day till the maximal tolerable dosage has been reached. In case of moderate renal insufficiency (Crea-tinin-Clearance 40-60 ml/min/1.73 m2) the maximal dosage is reduced to 10 mg daily. The treatment with memantine hydrochloride will be continued for one year and during this time all adverse events due to sickle cell anemia and possible side effects of the treatment are monitored. These data are compared with the history of the patient under best supportive care during the year before inclusion in the study. Endpoints of the study are severity and frequency of adverse events due to sickle cell anemia and tolerability of the treatment with memantine hydrochloride.

The invention claimed is:

1. A method for reducing the severity and frequency of adverse events in a mammal due to sickle cell anemia comprising administering an effective amount of MK-801 or memantine to a mammal in need thereof.

2. The method of claim 1, wherein MK-801 is administered to the mammal.

3. The method of claim 1, wherein memantine is administered to the mammal.

4. The method of claim 1, wherein the mammal is a human.

5. A method for reducing the severity and frequency of sickle cell crises in a mammal comprising administering an effective amount of MK-801 or memantine to a mammal in need thereof.

6. The method of claim 5, wherein MK-801 is administered to the mammal.

7. The method of claim 5, wherein memantine is administered to the mammal.

8. The method of claim 5, wherein the mammal is a human.

* * * * *